(12) United States Patent
Marshall et al.

(10) Patent No.: US 7,087,398 B2
(45) Date of Patent: Aug. 8, 2006

(54) METHOD FOR DETECTING UREASE

(76) Inventors: Barry J. Marshall, 40 Beatrice Road, Dalkeith, West Australia 6027 (AU); Aruni H. W. Mendis, 109 Fairway Cir., Connolly, West Australia 6027 (AU); Simon Chairman, 18 Retreat Circuit, Beaconsfield, Victoria 3807 (AU)

( * ) Notice: Subject to any disclaimer, the term of this patent is extended or adjusted under 35 U.S.C. 154(b) by 177 days.

(21) Appl. No.: 09/977,555

(22) Filed: Oct. 15, 2001

(65) Prior Publication Data

US 2003/0077680 A1 Apr. 24, 2003

(51) Int. Cl.
*C12Q 1/58* (2006.01)

(52) U.S. Cl. .......................................... 435/12
(58) Field of Classification Search .................... 435/12
See application file for complete search history.

(56) References Cited

U.S. PATENT DOCUMENTS

| | | | | |
|---|---|---|---|---|
| 4,748,113 | A | * 5/1988 | Marshall | 435/12 |
| 4,829,006 | A | 5/1989 | Smith et al. | |
| 5,314,804 | A | * 5/1994 | Boguslaski et al. | 435/12 |
| 5,498,528 | A | * 3/1996 | King | 435/34 |
| 5,679,570 | A | 10/1997 | Heckenmuller et al. | |
| 5,782,951 | A | 7/1998 | Aylen et al. | |
| 5,846,488 | A | 12/1998 | Richardson | |
| 2003/0077684 | A1 * | 4/2003 | Marshall et al. | 435/18 |
| 2003/0082661 | A1 * | 5/2003 | McMichael et al. | 435/12 |
| 2003/0082664 | A1 * | 5/2003 | Marshall et al. | 435/18 |

FOREIGN PATENT DOCUMENTS

| | | | |
|---|---|---|---|
| DE | 0 369 292 A1 | * | 11/1989 |
| EP | 0369292 A1 | | 5/1990 |
| EP | 0896547 | | 11/1997 |
| FR | 2654436 A1 | | 5/1991 |
| WO | WO 0164543 A1 | | 9/2001 |

OTHER PUBLICATIONS

Article—*Development of a Chemiluminescent Urease Activity Assay for Helicobacter pylori Infection Diagnosis in Gastric Mucosa Biopsies*, Aldo Roda, Francesco Piazza, Patrizia Pasini, Mario Baraldini, Laura Zambonin, Stefania Fossi, Franco Bazzoli, and Enrico Roda, Analytical Biochemistry, vol. 264, 1998, pp. 47–52.

* cited by examiner

Primary Examiner—Ralph Gitomer
(74) Attorney, Agent, or Firm—Jagtiani & Guttag

(57) ABSTRACT

A system and method for detecting bacterial infections in the gastrointestinal tract is disclosed. In one embodiment, the system includes a first composition separated from a second composition. The first composition contains urea in powdered form. The second composition, on the other hand, contains an indicator. A biopsy of a gastric sample is first contacted with the first composition and then placed in the second composition. The second composition indicates the presence of an enzyme that, in turn, indicates the presence of bacteria. In an alternative embodiment of the present invention, a biopsy of a gastric sample is contacted with a single composition. The composition contains urea in a powdered form combined with a dry indicator. Besides urea and a dry indicator, the composition can also contain an anti-caking agent.

17 Claims, 2 Drawing Sheets

METHOD FOR DETECTING UREASE

BACKGROUND OF THE INVENTION

Many ailments of the gastrointestinal system in humans are caused at least in part by bacteria. Such bacteria include those of the genus *Campylobacter*, and particularly *Helicobacter pylori*. For example, *Helicobacter pylori* can cause bacterial infections on the mucosal surface of the gastrointestinal tract, particularly on the surface of the stomach. The chronic disorders of the gastrointestinal system that can be caused by bacteria include peptic ulcers, gastritis, and the like.

Once a patient is showing symptoms of a gastrointestinal disorder, several tests can be used to diagnose the disorder, including the diagnosis of a possible bacterial infection. In the past, various tests have been proposed for the detection of *Helicobacter pylori*. One such test that has gained wide spread popularity and has provided many advancements in the early detection of gastrointestinal disorders is disclosed in U.S. Pat. No. 4,748,113, which is incorporated herein by reference. In the '113 patent, the presence of *Helicobacter pylori* in a gastric sample is detected by testing for the presence of an enzyme, specifically urease, which is produced by *Helicobacter pylori* in large amounts.

Urease is known to convert urea into ammonium carbonate, which then decomposes into ammonia and carbon dioxide. Consequently, in the past, one test for detecting the presence of *Helicobacter pylori* included the steps of contacting a sample of gastric material with a composition containing urea and an indicator, namely a pH indicator that changes color when there is a rise in pH. If urease is present within the gastric material it breaks down the urea, which results in the formation of ammonia after further decomposition and causes the pH indicator to change color.

The gastric material that is collected from the patient is typically a biopsy specimen that is removed from the gastric mucosa at endoscopy by means of biopsy forceps. Typically, the tissue sample is inserted into a gel that contains urea and the indicator.

Although the above method has provided great advancements in the early detection of gastrointestinal disorders, the testing composition used to detect the presence of urease has a limited shelf life. In particular, the urea and other reagents contained within the composition can have a tendency to degrade over time. Consequently, once formulated, the testing composition should be used in a relatively short amount of time and is also typically refrigerated prior to use in order to prevent degradation.

In view of the above, a need currently exists for an improved testing composition and associated method for the detection of bacterial infections in the gastrointestinal tract of patients. More particularly, a need exists for a composition for detecting urease in gastric samples that has a prolonged shelf life.

SUMMARY OF THE INVENTION

The present invention is directed to further improvements in the detection of bacterial infections in the gastrointestinal tract. In one embodiment, for instance, the present invention is directed to a system for detecting the presence of urease in a gastric sample in order to indicate the presence of *Helicobacter pylori*. The system includes a first composition that is maintained separate from a second composition for sequential contact with the sample. The first composition includes urea in a dried and finely powdered state. The urea is capable of being converted into ammonia when contacted with urease. The powdered urea can have a mean particle size of less than about 0.1 mm, and particularly less than about 0.05 mm. Besides urea, the first composition can also include other powder-like components, such as an anti-caking agent to prevent the fine urea from clumping or "caking".

The second composition, on the other hand, can contain an indicator and can be configured to indicate the presence of ammonia. For instance, the indicator can be a pH indicator that changes color when the pH of the second composition is increased to a certain level. For example, the indicator can be phenol red, which changes from yellow to red when exposed to a pH of greater than about 6.8.

In accordance with the present invention, the gastric biopsy sample is first contacted with the first composition. The urea powder contacts and sticks to the gastric biopsy sample. Should the gastric sample contain urease, the urea is converted into ammonia.

After contacting the first composition, the gastric material is then contacted with the second composition containing the indicator. The indicator indicates the presence of ammonia that, in turn, is a positive test for the detection of urease.

By maintaining the first composition containing urea separate from the second composition containing an indicator, various advantages and benefits are realized. In particular, the urea remains more stable and therefore the system has an increased shelf life. Further, the gel mixture is stable during manufacture so that much larger and longer duration production runs can be made without concern for slight temperature variations during the process.

Besides containing an indicator, the second composition can contain various other ingredients. For example, the second composition can be in a gel-like state and can contain a gel, such as agar. To maintain a low pH in the second composition within desired limits, the second composition can also contain a pH adjuster, such as an acid or buffering agent. For example, in one embodiment, the pH adjuster can maintain the pH of the second composition in a range of from about 4.5 to about 6. The second composition can also contain a bactericide, which can inhibit the growth of other organisms.

The first and second compositions can be contained within separate containers or can be spaced apart in the same container. For example, in one embodiment, a container can be used that includes a first well and a second well. The first composition can be located in the first well, while the second composition can be located in the second well. The container can be made from plastic and can include a peelable top made from a film. The film can be substantially or completely water impermeable over the first well to prevent any moisture from contacting the urea.

In an alternative embodiment, the present invention is directed to a system for detecting the presence of urease in a gastric sample in which the gastric sample is contacted with a single composition. In this embodiment, the composition includes urea and a dry indicator.

The urea, which is capable of being converted into ammonia when contacted with urease, is present in a dried and finely powdered state. The urea can have a mean particle size of less than about 0.1 mm.

The dry indicator is configured to indicate the presence of ammonia. For instance, the indicator can be a pH indicator that changes color when the pH of the composition is increased above a certain level.

Besides urea and a dry indicator, the composition can further include an anti-caking agent and/or a bactericide.

In this embodiment, a gastric sample is contacted with the composition. Any liquids contained in the gastric sample can be used to activate the composition. Alternatively, a liquid, such as distilled water, can be added to the composition in conjunction with the gastric sample. If urease is present in the gastric sample, the urease breaks down urea into ammonia, which in turn activates the indicator.

The present invention is further directed to a material well suited for detecting the presence of urease in a gastric material for diagnosing gastrointestinal disorders. The material includes a composition in the form of a powder. The composition can include urea and an anti-caking agent. Optionally, the composition can further contain a dry indicator.

Other features and advantages of the present invention will be discussed in greater detail below.

BRIEF DESCRIPTION OF THE DRAWINGS

A full and enabling disclosure of the present invention, including the best mode thereof, to one of ordinary skill in the art is set forth more particularly in the remainder of the specification, including reference to the accompanying figures, in which.

Figure 1:
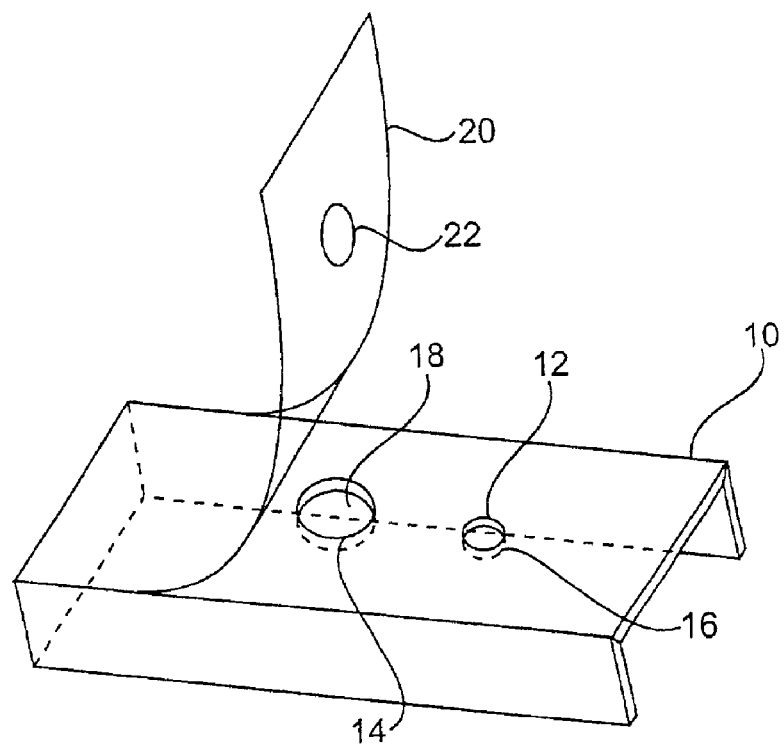
FIG. 1 is a perspective view of one embodiment of a system for detecting urease in accordance with the present invention.

Repeated use of reference characters in the present specification and drawings is intended to represent same or analogous features or elements of the invention.

DETAILED DESCRIPTION OF EMBODIMENTS

Reference will now be made in detail to the embodiments of the invention, one or more examples of which are set forth below. Each example is provided by way of explanation, not limitation of the invention. In fact, it will be apparent to those of ordinary skill in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

The present invention is generally directed to a system and method for the detection of gastrointestinal disorders caused by bacterial infections. More particularly, the system and method of the present invention detect the presence of urease on a gastric biopsy sample. Urease is an enzyme known to be produced by bacteria that are harmful to the gastrointestinal tract, including bacteria such as *Helicobacter pylori*. Gastrointestinal disorders that can be caused by bacterial infections include chronic or atrophic gastritis, gastroenteritis, non-ulcer dyspepsia, esophageal reflux disease, gastric motility disorders, peptic ulcers including gastric and duodenal ulcers, and the like.

In the past, in order to detect bacterial infections in the gastrointestinal tract, a biopsy sample of gastric material was first obtained. The biopsy sample was then contacted with a composition containing urea and an indicator, such as a pH indicator. If urease were present in the biopsy sample, the urease would break down and convert the urea in the composition to ammonia subsequently causing a rise in the pH of the composition. The rise in pH then caused the indicator to undergo a color change.

As described above, however, the composition containing urea and the indicator has a relatively short shelf life due to the instability of various ingredients in the composition, including the urea. The present invention is directed to an improved test for gastrointestinal disorders caused by bacterial infections. According to the present invention, in order to improve the shelf life of systems and devices designed to detect bacterial infections in the gastrointestinal tract, a composition containing urea is separated from a composition containing an indicator. The two compositions are then sequentially contacted with a biopsy sample in order to detect the presence of urease.

More particularly, the first composition contains urea in a finely powdered, dry state. By maintaining urea in a powdered form separate from the agar and the indicator, the urea remains more stable. Further, by maintaining the urea separate from the indicator, the handling requirements of the test system become more relaxed. For instance, by maintaining both compositions separate, there is no need to refrigerate the compositions prior to use or during shipping.

By maintaining the urea separate from the indicator composition, the process conditions for manufacturing the indicator composition also become relaxed. In particular, the indicator composition, such as an indicator gel, is much more stable during manufacture, allowing larger batches to be produced that are not sensitive to ingredients contained within the composition and to temperature variations.

Figure 2:
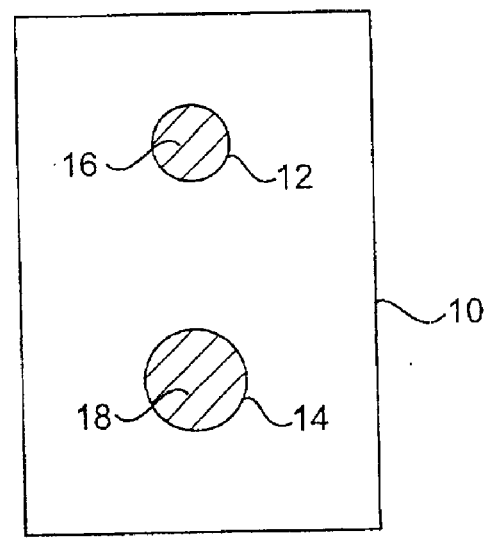
FIG. 2 is a top view of the system illustrated in FIG. 1.
Figure 3:
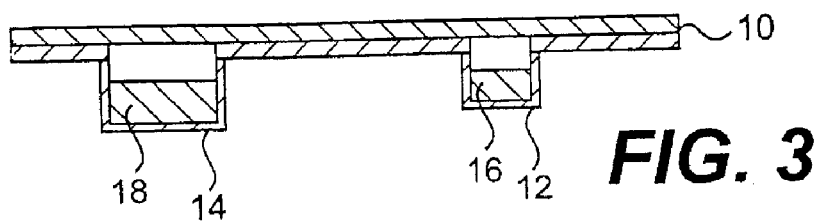
FIG. 3 is a cross-sectional view of the system illustrated in FIG. 1.

Although the system of the present invention for detecting urease can come in many forms, for purposes of explanation FIGS. 1–3 illustrate one exemplary embodiment of a device for detecting urease in biopsy samples in accordance with the present invention. As shown, the testing device in this embodiment includes a single container 10 defining a first well 12 and a second well 14. Contained in the first well 12 is a first composition 16 containing urea, such as urea in a finely powdered state with or without an anti-caking agent.

In the second well 14, on the other hand, is a second composition 18 containing an indicator. The indicator is configured to detect the presence of ammonia.

In this embodiment, the device 10 further includes a removable top 20 that covers the first well 12 and the second well 14. For example, the top 20 can be made from a plastic film. The top 20 is provided in order to prevent the first composition 16 or the second composition 18 from spilling or becoming contaminated prior to use.

In order to protect the powdered urea, the film top 20 can be made liquid impermeable at a location over the first well 12. In particular, the entire film top 20 can be liquid impermeable or, alternatively, a separate membrane 22 as shown in FIG. 1 can be placed over the first well 12 that is liquid impermeable.

Besides or in addition to making the top film 20 liquid impermeable, the membrane 22 can also be used to prevent urea particles from sticking to the film top when the film top is removed.

In order to perform a urease test using the device shown in FIG. 1, a biopsy sample is first taken from the lining of the gastrointestinal tract of a patient, such as from the lining of the stomach. The biopsy sample can be taken at endoscopy using biopsy forceps. The top film 20 is peeled back to expose the first composition 16 in the first well 12. The biopsy sample is then contacted with the first composition causing the urea powder to stick to the sample. For example, the biopsy sample can be rolled in the first composition much like the process of "flouring" a food product prior to cooking.

Once the first composition has coated the biopsy sample, the sample is then contacted with the second composition 18 containing an indicator located in the second well 14. Once contacted with the second composition, the powdered urea on the surface of the biopsy sample is moistened and activated by the second composition. Once moistened, the urea powder becomes available in greater amounts to any urease enzyme present in the biopsy sample. If present, the urease converts the urea into the unstable ammonium bicarbonate, which further decomposes into ammonia and carbon dioxide. The indicator present in the second composition indicates the presence of ammonia to signify a positive test for urease. For example, in one embodiment the indicator can be a pH indicator that changes color when the pH of its environment is increased.

Besides being contained within a single container as shown in FIG. 1, however, it should be understood that the first and second compositions of the present invention can be maintained in any suitable separated state prior to testing. In this regard, the first composition and the second composition can be maintained in separate containers if desired.

The ingredients that can be contained in the first composition and the second composition in accordance with the present invention will now be described in greater detail. As described above, the first composition is generally a dry or moisture-free composition containing urea in a powdered state. Urea has the chemical formula $H_2NCONH_2$ and is a naturally occurring product of protein metabolism. When contacted with urease, urea hydrolyzes to form unstable ammonium bicarbonate, which further decomposes into ammonia and carbon dioxide.

Urea in a powdered state for use in the present invention is available from various commercial sources. The particle size of the urea contained in the first composition is generally not critical although smaller particle sizes work more efficiently. In this regard, if desired, the urea can be ground to have a mean particle size of less than about 0.1 mm, particularly less than 0.05 mm, and more particularly less than about 0.01 mm. It should be understood, however, that even smaller particle sizes may be used. For example, in one embodiment, the urea particles can have a mean particle size of less than 3 microns, and particularly less than 1 micron. By reducing the particle size, more surface area of urea is available for reaction with urease and the urea will better stick to the biopsy sample.

When using relatively smaller particles, the urea particles can have a particle size distribution such that no particles present have a size greater than about 100 microns, particularly no greater than about 10 microns, and more particularly no greater than about 5 microns. The particle size of the urea can be determined using any suitable method, such as by using transmission electron microscopy (TEM). When using transmission electron microscopy, the average diameter of each particle is measured, followed by calculating the mean diameter of the urea particles in a particular group. The average diameter of each particle can be calculated by taking the average of the smallest diameter of the particle and the largest diameter of the particle. Besides transmission electron microscopy, light scattering can also be used to determine particle sizes. The mean particle size of the urea particles in a particular group is calculated by adding the sizes of the particles together and dividing by the number of particles.

Besides containing urea, the first composition can also contain various other dry additives. For example, in one embodiment, if desired, an anti-caking agent can also be contained within the first composition. The anti-caking agent will prevent the fine urea powder from clumping or "caking". Any suitable anti-caking agent can be used in the present invention. For example, in one embodiment, fine silicon dioxide or fine sodium alumino silicate powder can be contained in the first composition. The weight per weight (w/w) ratio of urea/silicon dioxide contained in the first composition can be any ratio from 1/1 to 100/1. The particle size of the anti-caking agent can vary depending upon the particular application. For instance, in one embodiment, the particle size of the anti-caking agent is no greater than the particle size of the urea.

The second composition, which is maintained separate from the first composition, contains an indicator for indicating the presence of ammonia. In general, any suitable indicator can be present in the second composition. In one embodiment, a pH indicator can be used that indicates a change in pH. For example, various pH indicators are available that change color as the pH is increased.

In general, when using a pH indicator, the pH of the second composition should be less than about 6.5. More particularly, the second composition can have a pH that is consistent with mammalian tissue, which typically has a pH of about 6.5.

In this regard, the pH of the second composition should be from 4.0 to 6.5, and particularly from about 4.5 to about 6.0. In this manner, when the second composition is contacted with the biopsy sample containing urea, the pH of the second composition will increase if the urea is being converted into ammonia. This rise in pH will then cause the pH indicator to signify a positive reading, such as by changing color.

The pH of the second composition should be adjusted to have a pH of from about 0.5 pH unit to about 2 pH units lower than that necessary for a color change to occur.

Consequently, when using a pH indicator, the indicator should undergo a color change or otherwise signify a positive reading when the pH of the second composition rises above neutral, and particularly above about 7.5. pH indicators useful in the present invention include indicators that undergo a change in color over a pH range of from about 5.5 to about 9.0, and particularly from about 6.5 to about 8.5.

One particular pH indicator that can be used in the present invention is phenol red. Phenol red changes from a yellow color to a red color as the pH of its surroundings increase. Phenol red is also referred to as phenolsulfonphthalein.

Other pH indicators that may be used in the present invention include p-nitro-phenol, bromthymol blue (dibromthymolsulfonph-thalein), neutral red (2-methyl-3-amino-6-dimethylaminophenazine), quino-line blue (cyanine), cresol red (o-cresolsulfonphthalein), matacresol purple (m-cresolsulfonphthalein), thymol blue (thymolsulfonphthalein), bromocresol purple (4,4'-(3H-2,1-benzoxathiol-3-ylidene)bis[2-bromo-6-methylphenol] S,S-dioxide), chlorophenol red, bromocresol green (4,4'-(3H-2,1-benzoxathiol-3-ylidene)bis[2,6-dibromo-3-methylphenol] S,S-dioxide), and bromophenol blue (4,4'-(3H-2,1-benzoxathiol-3-ylidene)bis[2,6-dibromophenol] S,S-dioxide).

In one embodiment, a combination of indicators can be used, such as described in U.S. Pat. No. 5,439,801 to Jackson, which is incorporated herein by reference. For example, in one embodiment, methyl red can be combined with bromthymol blue.

The second composition can be made up entirely of the indicator or can include other ingredients as desired. For example, in one embodiment, the indicator can be present in a gel-like material. In this regard, the indicator can be combined with a gelling agent so that the second composition is in a semi-solid state under ambient conditions.

In one embodiment, the gelling agent can be agar. Agar is a polysaccharide complex that is extracted from agarocytes of certain algae. Agar is available from various commercial sources. For most applications, the agar or any other gelling agent used should be nonnutritive, i.e., does not support the growth of microorganisms.

Besides, or in addition to, a gelling agent, an indicator can also be combined with a pH adjuster to maintain the pH of the second composition within preset limits. The addition of a pH adjuster is particularly beneficial when using a pH indicator to prevent against false readings. For example, as discussed above, the pH of the second composition should be from about 4.0 to about 6.5, when using a pH indicator. A suitable pH adjuster can be used to maintain the pH of the composition within this range. pH adjusters suitable for this test include acids and buffering agents. The use of a pH adjuster depends upon the make-up of the second composition and the requirements of the test. For example, reduction of the amount of buffer in the second composition leads to a much faster reaction and a faster change in colors by the indicator, with the most rapid reaction rate occurring in the absence of a buffering agent, as compared to the reaction rate when using a large amount of a buffering agent. Thus, if a high reaction rate is required, the use of buffering agents as pH adjusters should be limited.

In general, any suitable pH adjuster can be used, depending upon the requirements of the test and the second composition, including the use of acids and buffering agents such as sodium citrate, phosphate-citrate, citric acid, sulfamic acid, sodium bisulfate, sodium acetate, sodium phosphate, and potassium phosphate.

Another ingredient that may be contained in the second composition is a bactericide or a bacteristat. The bactericide or bacteristat can be used to act as a preservative for any of the other ingredients or can be used to substantially inhibit the growth of other organisms to prevent against false readings. Bactericides that can be used in the present invention include sodium azide, methyl paraben (methyl p-hydroxybenzoate), and propyl paraben (propyl p-hydroxybenzoate).

The amount of each ingredient added to the second composition will depend upon the various circumstances and the desired result. Besides maintaining the indicator as a liquid or in a gel state, the indicator can also be contained in an absorbent substrate, such as a substrate made from pulp fibers including cardboard or paper. In this embodiment, the second composition can be dry and relatively moisture free. When using a paper substrate, however, extra water and distilled water, may need to be added to the second composition in combination with the biopsy sample in order to provide enough moisture to activate the indicator.

The following is an example of one formulation that can be used as the second composition in the system of the present invention. The pH of the solid gel will be between 4 and 6.5 and particularly between 4.5 and 6.0.

| Ingredient | Amount |
|---|---|
| Agar (Extra Pure Grade) | 1.0–50.0 g |
| Citric Acid | 0.001–1.0 g |
| Phenol Red | 0.001–2.0 g |
| Methylhydroxy Benzoate | 0.01–100.0 g |
| Distilled Water | |

When forming a one liter batch of the above composition, the ingredients can be added in the following amounts.

| Ingredient | Reference | Amount |
|---|---|---|
| Agar (Extra Pure Grade) | Merck Catalog #1.01615.9025 | 15.0 g |
| Citric Acid | Merck Catalog #1.00247.1000 | 0.0145 g |
| Phenol Red | Merck Catalog #1.07241.0025 | 0.110 g |
| Methyl Paraben | Merck Catalog #1.06757.5000 | 2.0 g |
| Distilled Water | — | 1000 mL |

In producing the above gel composition, the distilled water is first heated to 95° C. The phenol red powder is added while stirring the distilled water, and the agar is added in small amounts while the mixture is maintained at 95° C. The citric acid and methyl paraben are then added to the mixture. The bulk liquid is cooled to 50° C. and dispensed in an amount of 0.2 mL into the second well of the present invention.

The first well of the container can contain 5 to 50 mg of the first composition, and optimally 30 mg of the resulting fine powder mixture. In the preparation of the urea mixture of the first composition for use in the first well, crystalline extra pure urea (Merck Catalog #1.08486.5000) is mixed with silicon dioxide (Sigma Catalog #S-5631) at a weight-to-weight ratio from 1:1 to 100:1, and in one embodiment in a weight-to-weight ratio of 2:1. The mixture is subject to grinding until a fine powder mixture results.

Figure 4:
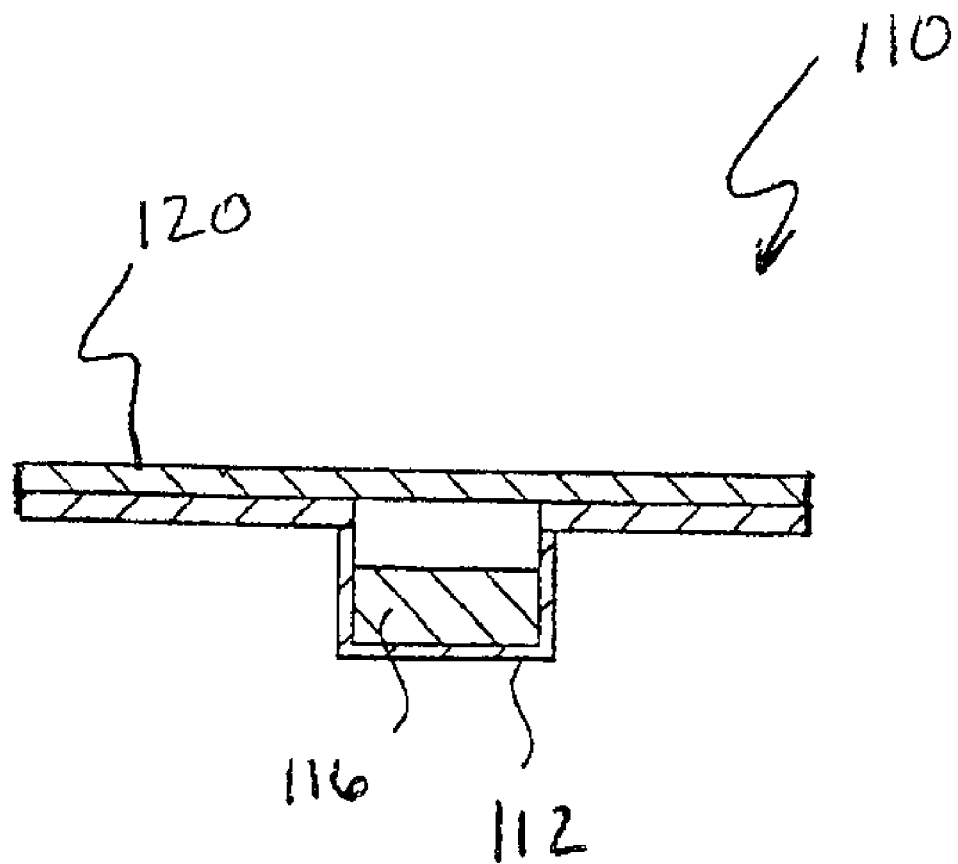
FIG. 4 is a cross-sectional view of another embodiment of a urease testing device made in accordance with the present invention.

Another embodiment of the present invention is illustrated in FIG. 4. In this embodiment, instead of containing two separate wells and two separate compositions, the urease testing device contains a single composition in a dry powdered state. Specifically, in this embodiment, the urease indicating composition contains dry powdered urea combined with a dry powdered indicator.

For example, as shown in FIG. 4, a urease testing device generally 110 includes a single well 112 covered by a peelable plastic film 120. In accordance with the present invention, the well 112 includes a urease indicating composition 116, which contains a powdered mixture of urea and an indicator.

The powdered urea contained within the well can be a urea as described above having an average particle size of less than about 0.1 mm, particularly less than about 0.05 mm, and more particularly less than about 0.01 mm. Combined with the powdered urea is a dry or powdered indicator, such as a pH indicator. In general, any suitable dry indicator can be present in the composition, such as any of the above-described indicators. The amount if indicator contained within the composition will generally depend upon the particular indicator chosen. Specifically, the indicator should be present in the composition in an amount sufficient to show a color change when the composition is contacted with urease present in a biopsy sample.

In this embodiment, the biopsy sample is placed in the well and mixed with the powdered composition. Any moisture present in the biopsy sample can be used to activate the urea and the indicator. If necessary, however, an aqueous solution, such as distilled water, can be added with the biopsy sample. If urease is present in the biopsy sample, the urease will convert the urea into ammonia which, in turn, will cause the indicator to indicate a positive result, such as by changing color.

If desired, an anti-caking agent as described above can also be contained in the dry powdered composition. In this embodiment, however, a pH adjuster or a bactericide will most likely not be needed, although both ingredients can be contained in the composition if desired.

EXAMPLE

The following example was performed in order to demonstrate the stability of a urease testing device made in accordance with the present invention.

A test slide according to the present invention was prepared containing the urea composition and the indicator gel composition described above. The indicator gel composition, however, did not contain the methyl paraben bactericide or the citric acid pH adjuster.

Specifically, the gel composition contained the following:

| Ingredient | Amount |
| --- | --- |
| Extra Pure Grade Agar | 1.4941 g |
| Phenol Red | 0.0110 g |
| Distilled Water | 100.00 mL |

The shelf life of the above prepared slide was then compared with the shelf life of a commercial product marketed under the name CLO-TEST by Ballard Medical/Kimberly Clark of Draper, Utah. The CLO-TEST product includes a urease indicator composition which contains a mixture of urea and an indicator in a gel as described in U.S. Pat. No. 4,748,113.

Three test slides made according to the present invention were compared with three samples of the CLO-TEST product. A standardized CLO-TEST Color Chart developed prior to the experiment was used to assign numerical scores to the color of the samples during the experiment.

The slides were affixed to a polystyrene box introduced into a chamber set at 37° C., 100% relative humidity, and 10% carbon dioxide. Photographs were taken every 24 hours for a period of 45 days, which were then assessed and given a score using the CLO-TEST Color Chart. Using color readings with scores of equal to or greater than 4 as unusable, the CLO-TEST samples were deemed unusable on day 4, while the test slides of the present invention were still viable on day 45.

The shelf life of the test slide of the present invention was also tested with an artificial biopsy by means of a tissue sample containing deliberately introduced urease. The artificial biopsy sample was placed in the first well containing the powdered urea. The sample was coated with urea, and then placed in the second well containing the indicator gel composition. Observations of the color change of the gel revealed it was still viable for the detection of ammonia after 39 days, when the gel was checked.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

What is claimed is:

1. A method for detecting a presence of urease in a gastrointestinal system comprising:

providing a sample of gastric material from a patient;

contacting said gastric material directly with a dry finely powdered first composition located in a first area, said first composition being urea, said urea converting to ammonia when contacted with urease;

coating said gastric material with said first composition, moisture in said gastric material causing said dry finely powdered first composition to stick to said gastric material;

removing at least a portion of said gastric material from said first area; and contacting said gastric material with a second composition located in a second area, said second composition comprising at least one indicator, said indicator being configured to indicate the presence of ammonia thereby indicating the presence of urease in said gastric material.

2. The method as defined in claim 1, wherein said urea has a mean particle size of less than 0.1 mm.

3. The method as defined in claim 1, wherein said first composition further comprises a dry, finely powdered anti-caking agent.

4. The method as defined in claim 1, wherein said second composition comprises a gel.

5. The method as defined in claim 1, wherein said second composition further comprises agar.

6. The method as defined in claim 1, wherein said indicator is a pH indicator that changes color when the pH is increased.

7. The method as defined in claim 1, wherein said urea has a mean particle size of less than about 0.05 mm.

8. The method as defined in claim 1, wherein said first composition and said second composition are positioned in the same container in a spaced apart relationship.

9. A method as defined in claim 1, wherein said second composition further comprises a bactericide or a bacteristat.

10. The method as defined in claim 1, wherein said indicator is phenol red.

11. The method as defined in claim 1, wherein said second composition further comprises a pH adjuster.

12. The method as defined in claim 2, wherein said second composition further comprises agar and a pH adjuster.

13. A method for detecting a presence of urease in a gastrointestinal system comprising the steps of:

providing a sample of gastric material from a patient;

contacting said gastric material directly with a composition comprising a dry, finely powdered urea and a dry, finely powdered, indicator, said urea converting into ammonia when contacted with urease and said indicator being configured to indicate the presence of ammonia coating said gastric material with said dry, finely powered urea and said dry finely powered indicator, moisture in said gastric material causing said dry, finely powered urea and said dry finely powered indicator to stick to said sample and activate said indicator, thereby indicating the presence of urease in said gastric material.

14. The method as defined in claim 13, wherein said urea present within said composition has a mean particle size of less than about 0.1 mm to increase efficiency.

15. The method as defined in claim 13, wherein said urea present within said composition has a mean particle size of less than about 0.05 mm to increase efficiency.

16. The method as defined in claim 13, wherein said composition further comprises an dry, finely powdered anti-caking agent.

17. The method as defined in claim 13, wherein said indicator comprises a pH indicator that changes color when the pH is increased.

* * * * *